United States Patent
Rullo et al.

[11] Patent Number: 6,083,153
[45] Date of Patent: *Jul. 4, 2000

[54] XIPHOID RETRACTION SYSTEM AND METHOD OF PERFORMING REOPERATIVE MIDSTERNOTOMY

[75] Inventors: Janice Lee Rullo, Mayfield Heights; William John Koteles, Broadview Heights, both of Ohio

[73] Assignee: Rultract, Inc., Cleveland, Ohio

[*] Notice: This patent is subject to a terminal disclaimer.

[21] Appl. No.: 09/235,704

[22] Filed: Jan. 22, 1999

Related U.S. Application Data

[60] Provisional application No. 60/072,366, Jan. 23, 1998, provisional application No. 60/072,240, Jan. 23, 1998, provisional application No. 60/072,273, Jan. 23, 1998, and provisional application No. 60/072,274, Jan. 23, 1998.

[51] Int. Cl.[7] .................................................. A61B 17/00

[52] U.S. Cl. ........................ 600/217; 600/227; 600/235

[58] Field of Search ................................. 600/201, 210, 600/217, 227, 228, 214, 226, 230, 231, 232, 234, 235

[56] References Cited

U.S. PATENT DOCUMENTS

| | | |
|---|---|---|
| 1,048,750 | 12/1912 | Smith . |
| 1,242,688 | 10/1917 | Hawley . |
| 1,914,202 | 6/1933 | Henze et al. . |
| 3,403,675 | 10/1968 | Carr . |
| 3,643,655 | 2/1972 | Peronti . |
| 3,710,783 | 1/1973 | Jascalevich . |
| 3,823,709 | 7/1974 | McGuire . |
| 4,143,652 | 3/1979 | Meier et al. . |
| 4,151,838 | 5/1979 | Crew ........................................ 600/217 |
| 4,622,955 | 11/1986 | Fakhrai . |
| 4,702,465 | 10/1987 | McConnell . |
| 4,865,019 | 9/1989 | Phillips ................................... 600/232 |
| 5,088,472 | 2/1992 | Fakhrai . |
| 5,938,592 | 8/1999 | Koteles et al. .......................... 600/228 |

FOREIGN PATENT DOCUMENTS 232451  12/1968  U.S.S.R. ............................... 600/226

OTHER PUBLICATIONS

KNY Scheerer Corp., Catalog of Surgical Instruments dated 1959, pp. 70–75 and 90–92.

The Surgical Armamentarium, V. Mueller, dated 1973, pp. 68, 281,346, 347.

The Surgical Armamentarium, American V. Mueller, dated 1980, pp. 74, 75, 78, 87.

Codman & Shurtleff, Inc. Catalog for Surgical Products dated 1984, pp. 431–437.

(List continued on next page.)

*Primary Examiner*—Jeffrey A. Smith
*Attorney, Agent, or Firm*—Renner, Otto, Boisselle & Sklar P.L.L.

[57] ABSTRACT

The present invention includes a set of rakes for use as surgical retractors in a surgical procedure in which the set of rakes includes a progressively longer body-supporting base portion. The present invention further includes a C-shape surgical retraction device including a rake end for lifting a first body portion, a pad end for depressing a second body portion and, e.g., a ring for attaching a lifting device, in which the device is adapted for use in a mid-cab surgical procedure. The present invention provides a set of rib rakes for retraction of the patient's ribs and thoracic region in a mid-cab procedure, in which each retractor rake has a progressively larger body-supporting portion, for providing additional support as the surgical cavity is enlarged during the course of dissection of, e.g., the internal mammary artery during its harvest for use in a coronary bypass procedure. The present invention provides as a retraction device a xiphoid rake for providing support to a body portion in a surgical procedure which includes forming a surgical cavity by a xiphoid entry, wherein the xiphoid rake is substantially stronger than conventional retractor rakes and provides a large body-supporting portion for providing greater sternal support as required in the surgical procedure.

11 Claims, 12 Drawing Sheets

OTHER PUBLICATIONS

Rultract Incorporated, Circulator Applied Internal Mammary Artery Retractor advertisement (undated).

Transaxillary Approach for First Rib Resection to Relieve Thoracic Outlet Syndrome, David B. Roos, M.D., from the Department of Surgery, University of Colorado School of Medicine, Annals of Surgery, Mar. 1966.

Thoracic Outlet Syndrome, David B. Roos, M.D. and J. Cuthbert Owens, M.D., Arch Surg—vol. 93, Jul. 1966.

"Stainless Steel Retractors" (Brochure), Scanlan–Morris Company, Stille Division, Madison WI, Product No. 46–46, p. 3, Dec. 1939.

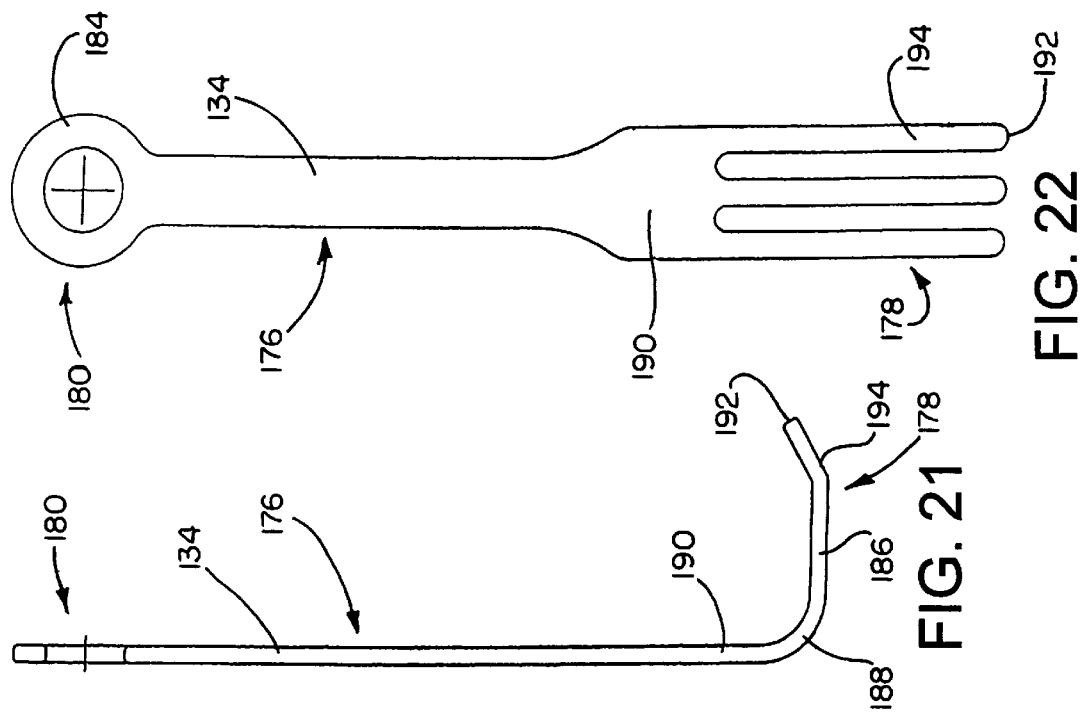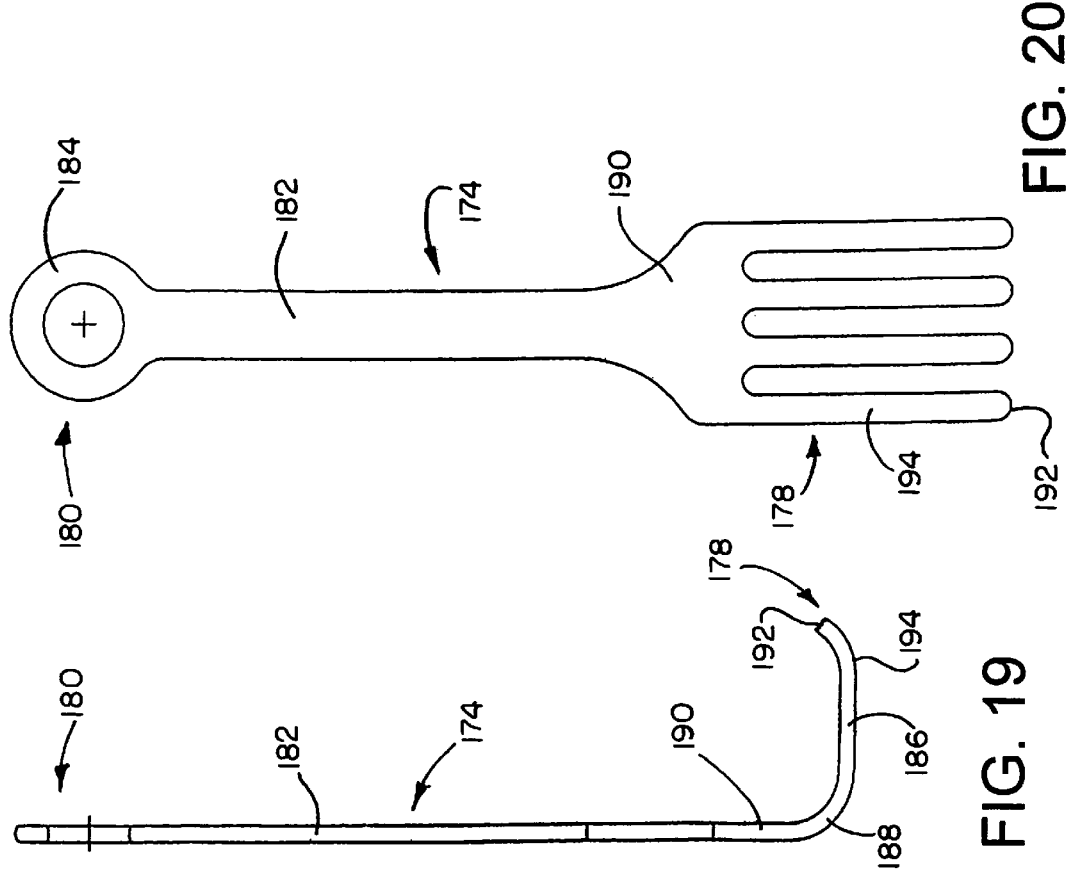

XIPHOID RETRACTION SYSTEM AND METHOD OF PERFORMING REOPERATIVE MIDSTERNOTOMY

CROSS-REFERENCE TO RELATED APPLICATIONS

Reference is hereby made to the following applications co-pending herewith, the disclosure of each of which is hereby incorporated by reference in its entirety: SURGICAL SUPPORT APPARATUS WITH SPECIALIZED RAKES, Ser. No. 60/072,366; SURGICAL SUPPORT APPARATUS WITH CROSS BAR SUPPORT AND EXTENSION FOR RETRACTOR APPARATUS, Ser. No. 60/072,240; SURGICAL SUPPORT APPARATUS WITH ADJUSTABLE RAKE AND ADJUSTABLE CABLE LIFTING DISK, Ser. No. 60/072,273, and SURGICAL SUPPORT APPARATUS WITH A Z-SHAPED RAKE PLATE, Ser. No. 60/072,274 all filed Jan. 23, 1998.

CLAIM FOR PRIORITY

This application claims priority under 35 U.S.C. 119(e) based on previously filed applications Ser. No. 60/072,366, Ser. No. 60/072,240, Ser. No. 60/072,273 and Ser. No. 60/072,274, all of which were filed Jan. 23, 1998, and all of which are incorporated herein by reference in their entirety.

FIELD OF THE INVENTION

The present invention relates generally to surgical instruments for holding and elevating body parts and/or for maintaining a clear opening to a body area during surgery, particularly thoracic surgery. More specifically, the present invention relates to support apparatus upon which surgical devices, such as retractors and the like, may be operably mounted.

BACKGROUND OF THE INVENTION

In the performance of surgery in the chest cavity, generally referred to as thoracic surgery, it is desirable to hold open the surgical cavity to provide access to the organ or body part upon which the surgery is being performed. This is especially important in the case of cardiac surgeries. An early example of a surgical retractor for use in coronary bypass surgical procedures which include dissection of the internal mammary artery is disclosed in U.S. Pat. No. 4,622,955, which is incorporated herein by reference.

In the device of U.S. Pat. No. 4,622,955 plural rakes which engage the body and retract the surgical cavity formed by a midsternotomy are relatively fixedly positioned with respect to each other from a rod. The rod may be elevated or lowered as desired. However, there is no adjustment for the rakes relative to the rod, to each other or to the surgical cavity. Furthermore, the rakes are generally small having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well-known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in the performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Coronary Bypass Surgery: The Midsternotomy

Coronary bypass surgery, in which the internal mammary artery is harvested from the chest wall and used for anastomosis of a vessel to bypass poorly functioning coronary arteries, has been performed thousands of times and has become an almost routine procedure for cardiac surgeons. Since the inception and throughout the development of the procedure, coronary bypass surgery has required a midsternotomy to provide access to the heart and coronary arteries. In the midsternotomy, an initial incision is made from the manubrium of the sternum to a point toward the xiphoid. Next, the sternum is split down the middle by means of a reciprocating sternal saw in order to provide access to the coronary arteries and the internal mammary artery. It has been estimated that in 1988, some 350,000 midsternotomy procedures were performed for coronary bypass surgery.

In performing the coronary bypass procedure, following the midsternotomy, it is necessary to retract one side of the split sternum in order to gain access to the thoracic cavity, and particularly to the internal mammary artery. Either the left or right internal mammary artery may be harvested for the bypass, so either side of the chest may need to be retracted. Retractors have been developed in order to provide the requisite retraction of the split sternum. An early example is disclosed in U.S. Pat. No. 4,622,955. The RULTRACT® internal mammary artery retractor is a more advanced retractor which has been developed to provide left or right internal mammary artery exposure in the undersurface of the chest wall. The RULTRACT® internal mammary retractor has been extensively used in coronary bypass surgery. The RULTRACT® retractor is not limited to coronary bypass surgery, having been used in various other thoracic surgical procedures, such as lung reduction and pericardial drainage.

The RULTRACT® internal mammary retractors include a rake plate and two or possibly three rakes. Most frequently, in use the two rakes are applied to one side of the opening formed by a midsternotomy and the rake plate is attached to a lifting device. The lifting device lifts the rake plate and the rakes, applying an upward and outward retraction to the sternum by which the surgical cavity is opened. The sternum is securely held in the open position when the lifting device is locked in position. This exposes the entire course of the mammary artery from its origin to its bifurcation, allowing its dissection. The rakes in the conventional retractor have a relatively small radius of curvature and have quite sharp tips to provide a secure attachment to the sternum. With the sternum securely held in the open position, the coronary artery dissection may then be carried out by the surgeon. In the standard midsternotomy, the retractor provides good exposure and allows the surgeon sufficient access for the dissection of the mammary artery.

After the coronary artery has been harvested, the RULTRACT® retractor is removed and a sternal retractor is placed in the chest and the grafting and anastomoses is performed. Closure is normally accomplished in this procedure by applying wires or staples to the sternum to hold it together in the properly aligned position for healing.

The midsternotomy is a highly invasive procedure, and much of the difficulty in recovering from a coronary surgical procedure involving a midsternotomy is due to the trauma resulting from the midsternotomy rather than to any trauma inflicted upon the coronary arteries or other thoracic organs and structures. As a result, a need has been identified for a less invasive procedure which will provide the surgeon with access to the coronary and internal mammary arteries with a minimum of trauma to the thoracic region.

The Mid-Cab, A Less Invasive Procedure

A less invasive procedure which has been developed to provide access to the mammary artery and the coronary arteries for coronary bypass surgery is known as the mid-cab or minimally invasive technique. In the mid-cab, an incision is made between the third and fourth rib, in the third intercostal region. The fourth rib is released from the sternum, and the incision is retracted downward by attaching a retractor rake to the fourth rib. A second retractor rake is next attached to the third rib, which is retracted upward and in the cranial direction. With access thus provided to the third rib and in the direction of the upper chest, the surgeon is able to create an opening from the third rib to the first rib or subclavian region. Via this opening, the surgeon is provided with access to the mammary artery, which is progressively dissected from the chest wall as the opening is progressively advanced toward the first rib. With the development of this procedure, a need has been identified for more advanced retractors specially adapted to the mid-cab procedure, and particularly for a retractor which can simultaneously retract the third and fourth ribs in different directions.

It is well-known among cardiac surgeons that the position of the internal mammary artery in the chest is variable from patient to patient. For this reason, during the mid-cab procedure, it is sometimes necessary for the surgeon to manipulate the chest wall to provide adequate access to the mammary artery. The surgeon may have to either elevate or depress the chest wall in the region of the first rib in order to gain access to the mammary artery so that it can be dissected in this procedure. Thus, a need has been identified for devices which can assist the surgeon in the less invasive mid-cab procedure, particularly including a retractor capable of two-direction retraction at the site of the intercostal incision and devices for providing elevation and/or depression of the clavicle and first rib region of the chest wall.

Reoperative Coronary Bypass Surgery

As coronary surgery has become increasingly prevalent and postoperative coronary rehabilitation more successful, a larger number of patients are surviving longer than the expected patency of their graft conduits. This has resulted in an increasing number of patients having to undergo a second coronary bypass procedure. The second, or reoperative, procedure has sometimes been referred to as a "re-do" procedure. Unfortunately, the re-do midsternotomy is neither as simple nor as safe as the initial procedure. This is primarily due to the scarring and resultant adhesions which develop between the internal side of the sternum and the underlying organs and tissues of the thoracic cavity following the initial midsternotomy. When the re-do midsternotomy is performed by essentially repeating the steps of the initial procedure, an increase in morbidity and mortality has been observed. Thus, a need has arisen for an alternative procedure.

An alternative procedure which has been adapted to coronary surgery in order to avoid the dangers of the re-do midsternotomy is known as a xiphoid entry. In the xiphoid entry, an initial incision is made along the scar from the previous midsternotomy to a point midway between the xiphoid and the umbilicus. The old sternal wires are removed. The xiphoid process is excised. A single retractor rake is applied to the caudal end of the sternum and the sternum is firmly retracted in an anterior and cranial direction. This allows the surgeon to directly visualize the anterior retrosternal space, so that the retrosternal adhesions can be taken down. The surgeon progressively takes down the adhesions toward the subclavian, until the sternum is freed from the underlying organs. Once this is done, the retractor may be removed and the sternum divided with a reciprocating sternal saw as in the original procedure.

During the retraction, particular care must be exercised since, first, the quite sharp rake tips of the standard retractor are applied directly to the lower end of the sternum from which the xiphoid process was excised, and second, a very strong lifting force is required to elevate the entire sternum. The possibility of unintended trauma to the sternum exists. A second problem which has been experienced with the procedure described above is that the entire retractor plate and the extra, non-used rake must be suspended in a central location in the operating field, further obstructing the work area with its already limited available space. A third problem is that due to the rake plate and various parts attaching it to the lifting apparatus, the retraction force applied to the sternum is not transmitted in a simple straight line from the lifting apparatus to the sternum. See FIGS. 16 and 17. Thus, a need has been identified for a rake which is more appropriately adapted to the xiphoid entry in a re-do coronary bypass procedure.

In the procedures described in the foregoing and in additional thoracic surgical procedures, the surgeon may be required to adapt the support apparatus for retraction of the patient's body in several directions at once. In such an instance, a single retractor held by a single support device may not be sufficient to provide the retraction required by the surgeon. Furthermore, it may be helpful to the surgeon to combine various embodiments of retraction devices in order to adequately obtain the retraction required.

Accordingly, there is a strong need in the art to provide for surgical retractor rake apparatus with which to facilitate the development and implementation of new surgical procedures, particularly less invasive procedures such as the mid-cab coronary artery bypass procedure, and for more radical thoracic procedures, such as a lung reduction or other procedure.

SUMMARY OF THE INVENTION

The internal mammary artery is known to thoracic surgeons to not have a well-defined position in all patients, but rather to have a highly variable position in the thoracic cavity. As a result, the procedure for accessing and harvesting a portion of the internal mammary artery must be quite flexible, particularly in the mid-cab procedure. Several embodiments of the present invention relate to retraction devices which may be selected and quickly implemented as required in an individual surgical procedure depending on the particular patient's needs. The invention may allow the surgeon to perform a less invasive procedure while maintaining the option to easily change to the standard midsternotomy in the event of unforeseen difficulties. When the RULTRACT® retractor system and the device of the present invention are employed, the changeover to the midsternotomy may be made with a minimum change of retraction equipment.

According to an aspect of the present invention a series of novel rakes are useful as surgical retractors in the less invasive mid-cab coronary bypass procedures. According to an embodiment of the invention a C-shape rake (which also may be referred to as a C-rake) is useful for simultaneously retracting and depressing neighboring areas of a patient's chest, particularly during the mid-cab procedure. According to another embodiment of this invention a set of rib rakes for retracting a patient's chest wall during the mid-cab procedure includes rakes with progressively longer body-supporting portions for providing progressively greater support as the surgical cavity is enlarged during the process of dissecting the mammary artery from the chest wall.

According to another embodiment, a xiphoid rake useful as a surgical retractor in the reoperative or re-do midsternotomy is useful for retracting the entire sternum prior to the midsternotomy in a re-do coronary bypass procedure including a xiphoid entry when the initial coronary bypass also included a midsternotomy. The xiphoid rake may be employed when a mid-cab procedure must be converted to a standard midsternotomy, when the midsternotomy will be a re-do procedure.

According to an aspect of the invention the rakes may include a ring portion for attaching to a lifting device. According to another aspect, the lifting device includes a snap clip which provides for quick attachment and release of each rake. According to another aspect, the lifting device includes a swiveling hub attaching the snap clip to the lifting device.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 19 is a side elevational view of a first embodiment of a xiphoid rake in accordance with the invention;

FIG. 20 is a front elevational view of the xiphoid rake of FIG. 19 in its preformed flat state in accordance with the invention;

FIG. 21 is a side elevational view of a second embodiment of a xiphoid rake in accordance with the invention;

FIG. 22 is a front elevational view of the xiphoid rake of FIG. 21 in its preformed flat state in accordance with the invention.

DETAILED DESCRIPTION

Figure 1:
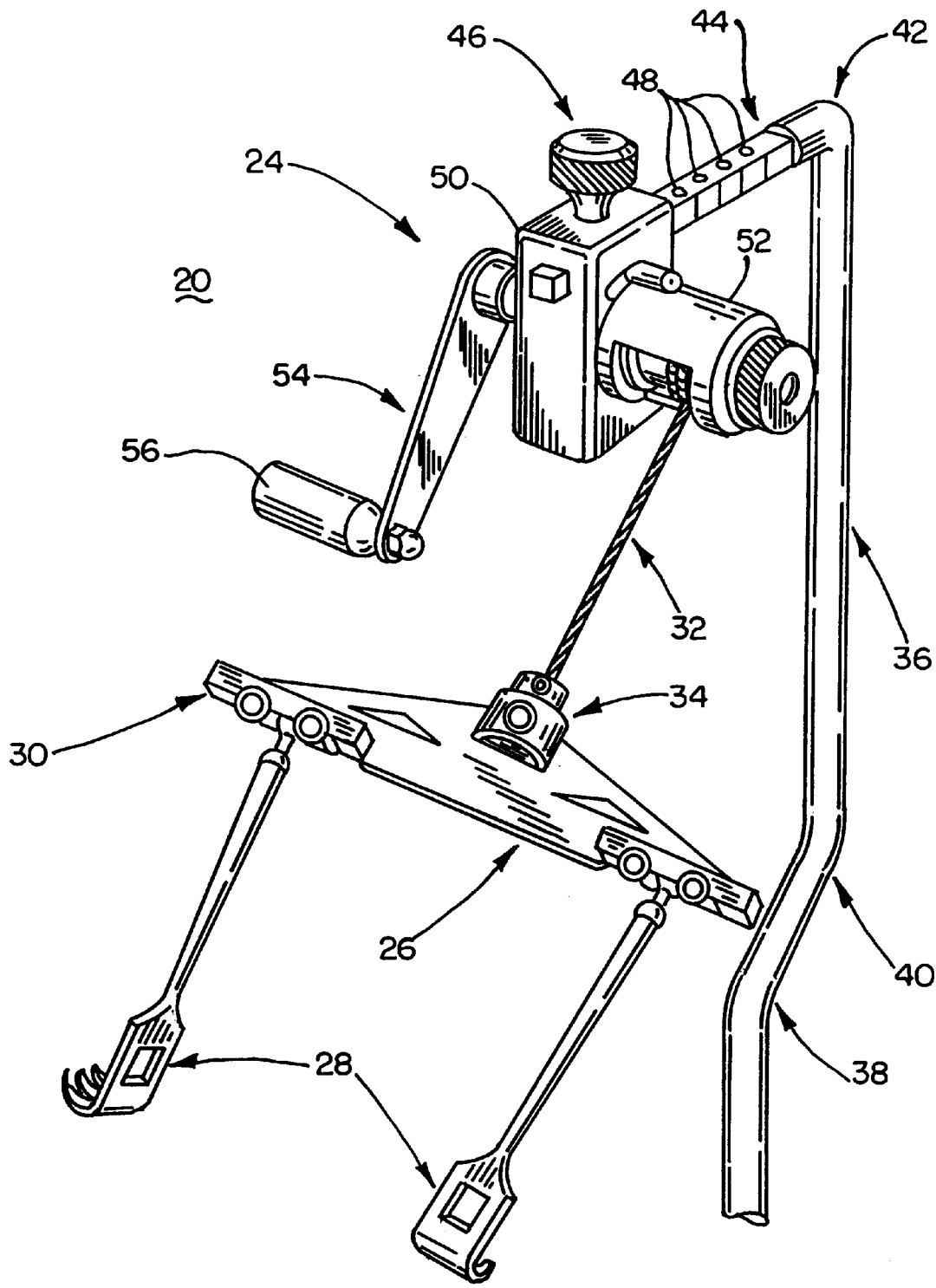
FIG. 1 is a perspective view of a conventional Rultract® surgical retractor.

The present invention will now be described with reference to the drawings wherein like reference numerals are used to refer to like elements throughout. As mentioned above, the present invention relates to surgical instruments for holding open a body part during surgery, for example, to maintain open and clear a surgical cavity during surgery, particularly including cardiac surgery or other thoracic surgery. In all embodiments described hereinafter, the preferred material of construction is stainless steel, preferably 304 stainless steel, which has good strength and sterilization characteristics and is resistant to corrosion even after many cycles of use, cleansing and sterilization.

Referring to FIG. 1, a conventional RULTRACT® retractor and surgical support assembly 20 are shown. The RULTRACT® retractor includes a ratcheting lifting device 24, a rake plate 26, at least one rake 28 for applying retraction to a patient's body, and pivoting mounting means 30 for mounting the rakes 28 to the rake plate 26. The rake plate 26 is attached to the ratcheting lifting device 24 by a cable 32. The cable 32 is attached to the rake plate 26 by a pivot hub connector 34.

The rake plate 26 and the rakes 28 associated therewith may be raised or lowered via the cable 32, which is connected to the lifting device 24. As described below, the RULTRACT® system preferably includes a ratcheting lifting device 24, although other lifting devices could be used. Preferably, a pivot hub connector 34 allows the rake plate 26 to rotate relative to the cable 32 to facilitate positioning of the rakes 28 relative to the surgical cavity of the patient without twisting the cable 32, which could result in a torque applied to the retractor rake plate 26, which undesirably could be transmitted to the patient's body.

In the conventional RULTRACT® retractor assembly 20, the ratcheting lifting device 24 is mounted on a support pole 36. Although not shown in FIG. 1, the support pole 36 is mounted at its lower end to a surgical table by conventional means. Preferably, the support pole 36 includes bends 38 and 40 which dispose outward the portion of the support pole 36 which is above the level of the surgical table so as to provide additional space in the surgical field around the patient. At the upper end of the pole 36, is a bend 42, preferably right-angled, connecting the support pole 36 to a horizontally extending portion 44. The horizontally extending portion 44 extends outwardly above the patient, so that the retraction force is applied at least partially in an upward direction. Since the ratcheting lifting device 24 is not aligned with the patient's midline, the retraction is applied partially, outwardly, laterally with respect to the patient.

In this embodiment, the ratcheting lifting device 24 is mounted on the horizontal extension 44. The lifting device 24 is provided with a securing bolt 46 by which the lifting device 24 is securely positioned on the extension 44. To facilitate quick and sure positioning of the lifting device 24 on the extension 44, a plurality of bores 48 are provided, into which an end of the securing bolt 46 may be inserted. The bores 48 allow for precise horizontal adjustment of the position of the lifting device 24 relative to the patient and the surgical field.

The ratcheting lifting device 24 preferably includes a ratcheting winch assembly 50 for reeling in the cable 32. The cable 32 is attached to and preferably is wrapped around a spool (not shown) extending outwardly from the ratcheting winch assembly 50. The spool around which the cable 32 wraps is preferably partially enclosed by a housing 52. The opposite end of the spool is attached to, and the winching assembly is actuated by, the crank arm 54 and crank handle 56, in conventional fashion.

The lifting device and support arm used in the present invention are preferably essentially the same as the conventional assembly described above and will not be further described except as necessary to indicate the functioning of the present invention relative thereto.

Figure 2:
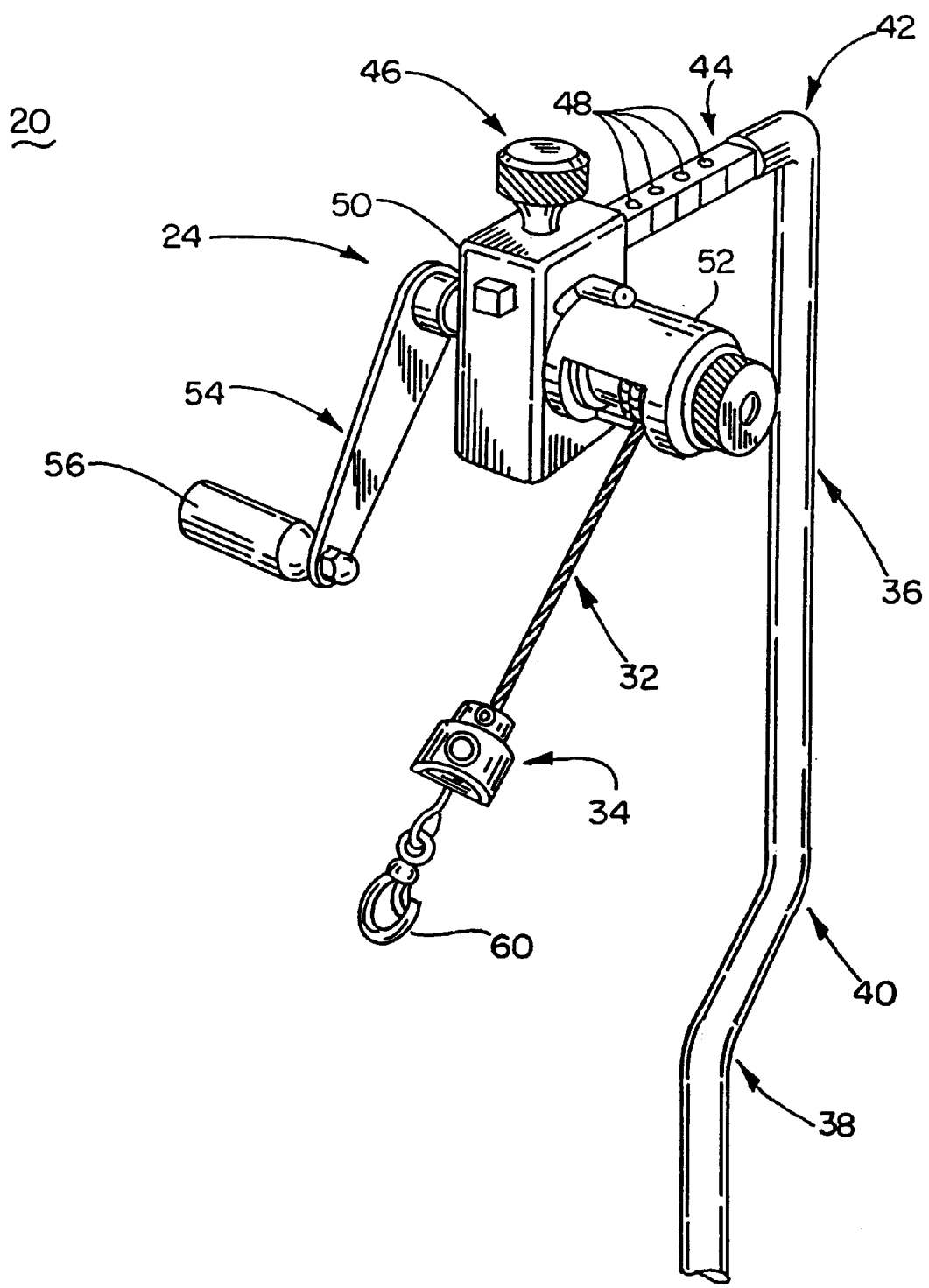
FIG. 2 is a perspective view of a conventional Rultract® retractor support and lifting apparatus with a swiveling hub and snap clip for attaching a rake plate or individual rakes.

Preferably, in the present invention, the ratcheting lifting device 24 is similar to the lifting device 24 shown in FIG. 1 and available from RULTRACT, INC., Cleveland, Ohio. Referring to FIG. 2, in an alternative embodiment of the surgical support assembly of the present invention, the ratcheting lifting device 24 has the cable 32 attached thereto, as described above with reference to FIG. 1. As shown in FIG. 2, the free end of the cable 32 may have attached thereto a pivot hub connector 34 and a snap ring 60. The snap ring 60 is preferably used for attaching the rakes or retraction apparatus to the cross bar assembly of the present invention. The snap ring 60 provides a secure, but quickly releasable attachment between the lifting device 24 and the rakes or retraction apparatus used with the present invention. Other quick-release devices known in the art may be substituted for the snap ring 60.

In each embodiment of the present invention, the rake preferably has a ring end and a rake end. The ring end preferably includes a ring which is used for attaching the rake to a lifting device. The ring may be substituted by other means for attaching a lifting device, but the ring is preferred for reasons of its greater strength relative to its weight, compared to other configurations.

However, other equivalent configurations may be used for the means for attaching a lifting device.

In a first embodiment of the present invention, (FIGS. 3–6) a C-shape rake, or C-rake, is provided. This embodiment relates to a device by which the surgeon, in a mid-cab procedure, is able to exert a downward force on the patient's first rib or clavicle area while simultaneously exerting an upward retracting or lifting force at or near the site of the incision, which, as disclosed above, is usually located at either the third, fourth or fifth intercostal region. Exerting such downward pressure is sometimes necessary to provide the surgeon access to the internal mammary artery, depending on the location of the artery in the particular patient.

In this first embodiment, the C-shape surgical retraction device includes a rake end for lifting a first body portion, a second pad end for depressing a second body portion and a means for attaching a lifting device. Preferably, the means for attaching a lifting device is a ring disposed adjacent or near the rake end of the C-shape retractor. Preferably, the first body portion is a third or fourth rib and the second body portion is the region around the clavicle and first rib. The C-shape retractor preferably is adapted for use in a mid-cab surgical procedure.

In the portion of the bypass procedure during which the mammary artery is harvested, it is necessary to dissect the mammary artery from the chest wall. In some patients, the surgeon has difficulty accessing the mammary artery without application of downward pressure on the upper portion of the patient's chest. The C-shape retractor provides the surgeon with the ability to press down on this upper region of the patient's chest when this becomes necessary during the dissection of the mammary artery. The C-shape retractor is preferably provided in several sizes, to allow the surgeon to adjust to the different chest sizes of different patients.

Figure 3A:
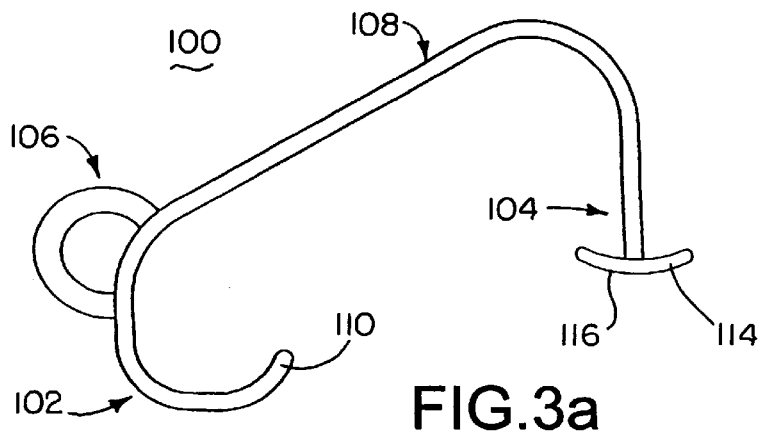
FIGS. 3a, 3b and 3c are side views of different sizes of a C-rake in accordance with an embodiment of the invention.
Figure 3B:
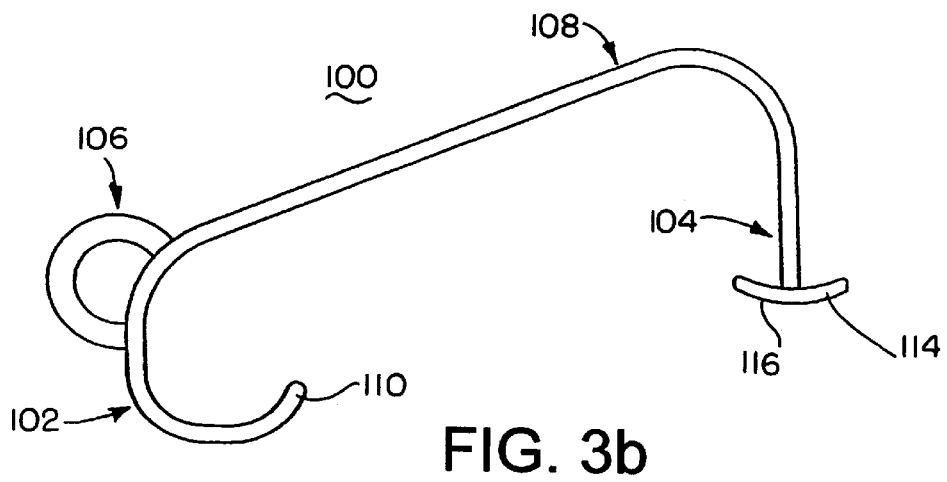
Figure 3C:
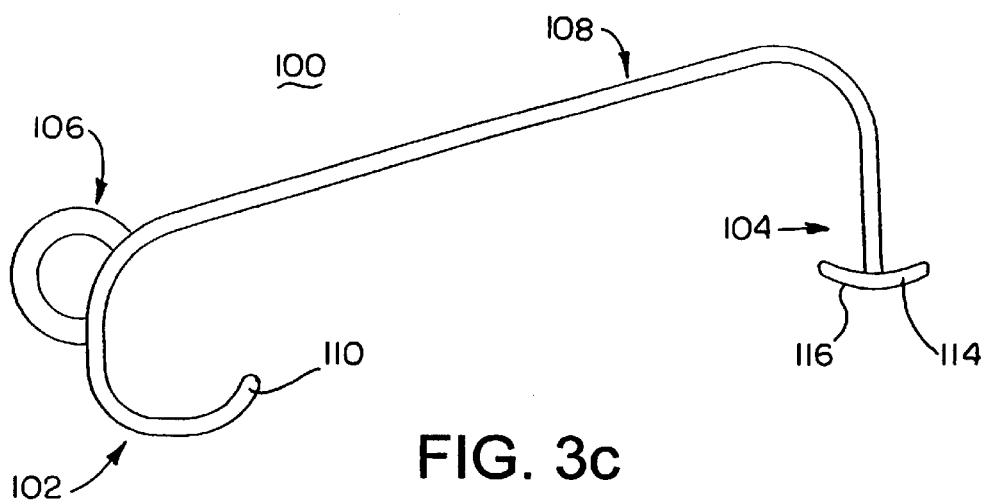
Figure 4A:
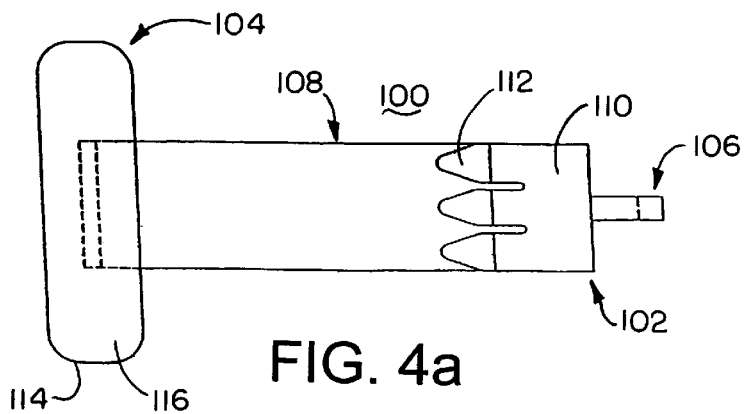
FIGS. 4a, 4b and 4c are front elevational views of the three sizes of the Crake of FIGS. 3a, 3b and 3c.
Figure 4B:
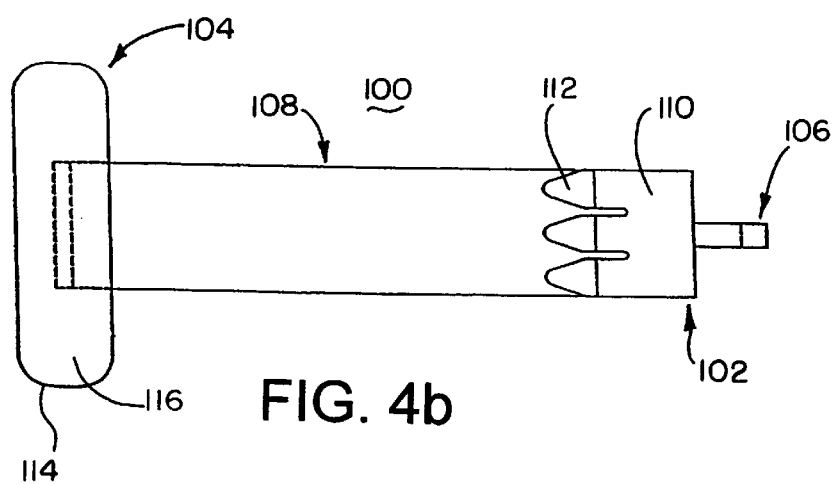
Figure 4C:
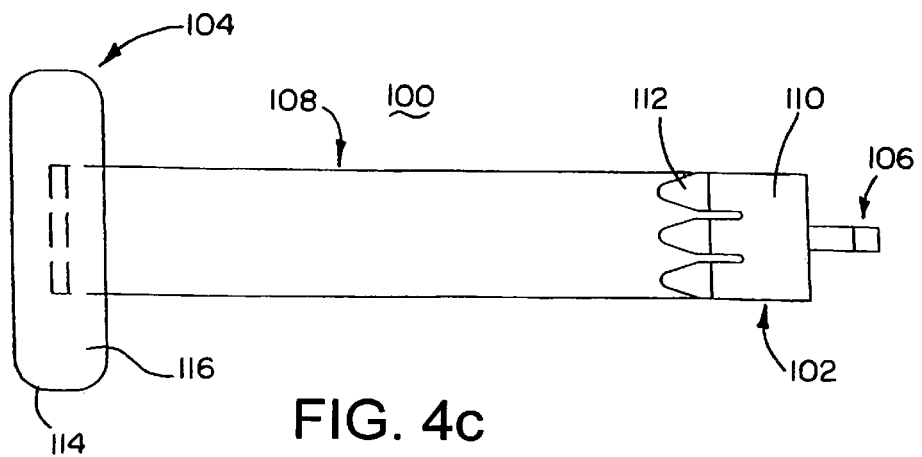
Figure 5:
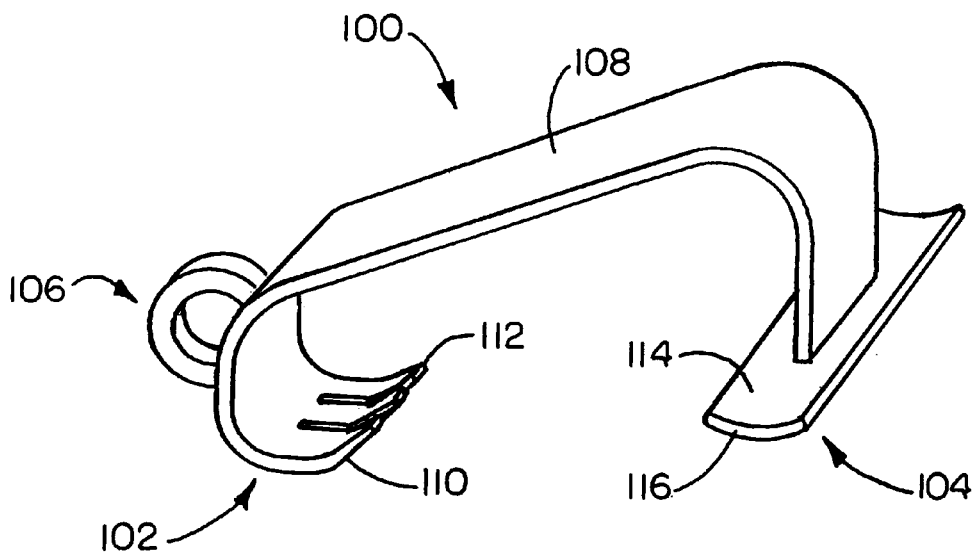
FIG. 5 is a perspective view of a C-rake in accordance with an embodiment of the invention.

In FIGS. 3–6, a C-shape surgical retraction device 100 is shown. The C-shape device, as best shown in FIGS. 3, 4 and 5, includes a rake end 102 for lifting a first body portion, a pad end 104 for depressing a second body portion and a ring 106 for attaching a lifting device. The device 100 further includes an arm 108 to which the rake end 102, the pad end 104 and the ring 106 are each either attached or integral therewith. FIGS. 3a, 3b and 3c, and 4a, 4b and 4c, show progressively longer and larger embodiments of the C-shape retraction device 100.

The rake end 102 includes a rake 110 having a plurality of rake teeth 112. Preferably, the rake 110 has at least three rake teeth 112, but may have more or fewer as required for a particular patient. A larger patient generally requires more or larger rake teeth 112.

The pad end 104 includes a pad 114 which is preferably about 2 cm. wide and about 6–7 cm. in length. The pad 114 includes a lower patient-contacting side 116. As with the rake 110 at the rake end 102, the pad 114 is preferably larger for larger patients. Preferably, as best shown in FIGS. 3 and 5, the pad 114 has a slight curvature such that the patient-contacting side 116 is convex.

The convexity of the pad 114 assures a minimum of trauma to the portion of the patient's body to which the downward force is applied.

Figure 6:
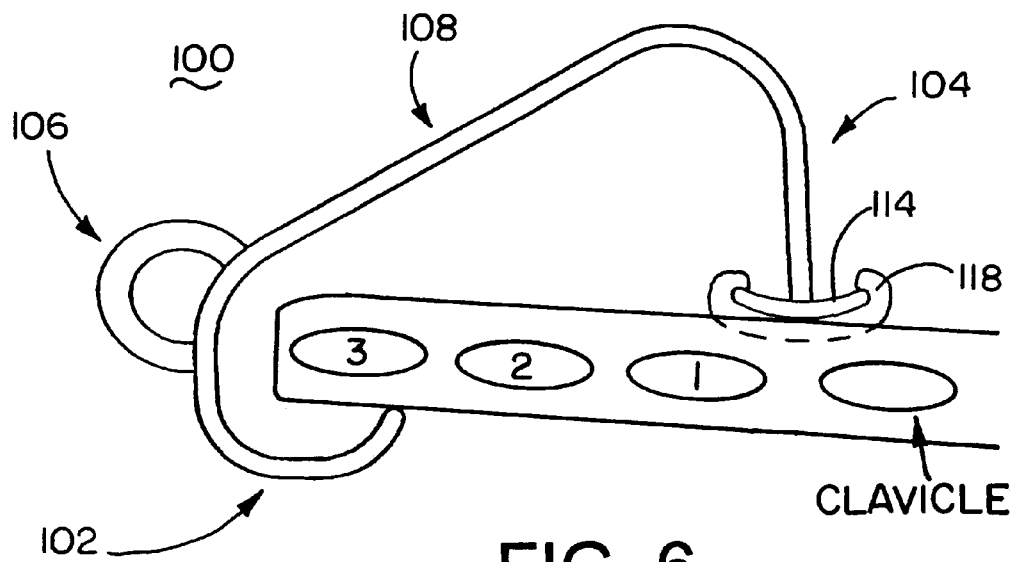
FIG. 6 is a schematic diagram of a C-rake in use in a patient's chest.

As shown in phantom in FIG. 6, the pad end 104 may be further provided with a sleeve or cover 118 made of a preferably non-metallic material. The sleeve 118 provides a larger patient-contacting area, thereby further avoiding possible trauma to the portion of the patient's body to which the downward force is applied. The sleeve 118 is most preferably made of a polymeric or thermoplastic material which may be provided in a sterile package and discarded after a single use. The sleeve 118 may be considerably larger than the example shown in FIG. 6, as desired by the surgeon.

The pad end 104 is connected to the rake end 102 by the arm 108. Preferably, the pad end 104 is integrally attached to the arm 108, preferably by means of a continuous weld, such that no seams, cracks, holes or other openings remain into which contaminants may collect and lodge, and to provide the greatest strength and durability to the C-shape retraction device 100. The arm 108 is preferably about 2–3 cm. in width and has a sufficient thickness to provide the strength required to provide the lifting and depressing forces for which it is intended, e.g., about 2 mm. thick. The thickness of the arm 108 may be increased as necessary. FIGS. 3a–3c best show the preferred curvature of the arm 108. As is most apparent in FIGS. 3 and 6, the rake end 102 is at a relatively lower position than is the pad end 104. This spatial relationship is preferred because in a supine patient the third intercostal region is at a higher position than is the clavicle. The length of the arm 108 may be varied as required to fit a particular patient, since the exact distance from the third intercostal region to the clavicle varies with the size of the patient. Generally, larger patients will require a longer arm 108.

As best shown in FIGS. 3 and 5, the ring 106 is attached to the arm 108 near the rake end 102 of the C-shape lifting device 100. The ring 106 is the preferred means for attaching the lifting device. Although not shown in the drawing figures, other equivalent attachment means, such as a hook, a partial ring, i.e., with a separation at some location in its circumference, or an opening which can accommodate insertion of a hook or clasp in the arm 106 of the device 100, may be alternatively and equivalently provided. Preferably, the ring 106 or alternative means is disposed adjacent the rake end 102, in a position to provide a desired lifting force to the patient's body via the rake 110. As described above relative to the pad 114, the ring is preferably integrally attached to the arm by a continuous weld, free of seams, cracks, pinholes and the like.

Preferably, as shown in FIG. 6, the first body portion of a patient, to which the rake end 102 is applied, is the patient's third or fourth rib and the second body portion of the patient, to which the pad end 104 tends to apply a downward force, is an area near the patient's clavicle. The C-shape retraction device 100 is adapted preferably for use in a mid-cab surgical procedure, but it may be useful in other procedures in which simultaneous lifting and depressing forces need to be applied to a patient's body during a thoracic surgical procedure.

It is noted that the downward force applied to the pad end 104 is actually only a relative force, in that no actual, directly downwardly applied force is exerted upon the pad end 104. This is due to the fact that the only force actually applied is the lifting force which is applied to the rake end 102. The rake end 102 is thereby lifted and the C-shape retraction device effectively pivots about a point centered on the pad 114. Thus, the lifting force is like a levering force, in which the fulcrum is the pad end 114, and the lifting force is applied to the end of the lever, which is the rake end 102.

The present invention further provides a method of simultaneously applying both an upward retracting or lifting force and a downward pressing force on a patient's chest area, preferably in a mid-cab procedure. The method includes the steps of making a surgical incision in an intercostal region of a patient's chest, providing a C-shape surgical retractor having a rake end and a pad end, applying the rake end of the C-shape retraction device to a rib adjacent the incision, applying the pad end of the C-shape retraction device to an area adjacent a first rib or clavicle of the patient, attaching a lifting device for applying a lifting force to the rake end of the C-shape retraction device, whereby the rib adjacent the incision is retracted to an elevated position and the area adjacent the first rib or clavicle is held in a relatively lower position. The method preferably includes a step of providing a pad and/or sleeve on the pad end prior to applying the C-shape retraction device to the patient's chest. As can be appreciated by the foregoing, the rake end of the C-shape retraction device is moved from a position that is relatively lower than the pad end to a position that is relatively higher than the pad end.

A second embodiment of the present invention provides a set of rib rakes for use as surgical retractors in a surgical procedure which includes forming a surgical cavity by a less invasive mid-cab procedure. The set of rakes of this embodiment is particularly useful for the steps of dissecting the internal mammary artery from the chest wall in the mid-cab procedure when it is not necessary to employ the C-shape retractor device of the first embodiment, or before or after using the C-shape retractor device.

In the second embodiment of the present invention, the set of rib rakes provides progressively increasing support as the chest cavity is enlarged from the initial incision near the third intercostal region towards the region of the first rib and the clavicle, during which time the internal mammary artery is being dissected from the chest wall. In the mid-cab procedure, as described in the background section, an initial intercostal incision is made, then the incision is gradually made deeper into the region under the ribs. The incision is deepened moving in a direction toward the first rib and the patient's head from the rib adjacent the incision, usually the third or fourth rib. As the incision is deepened, the surgeon is advantageously provided with additional lifting support for the ribs by progressively using longer reach rib rakes, switching from the shorter reach to the medium reach and then the long reach rib rake of the present invention. The rib rakes of the present invention provide this lifting force without the necessity of a surgical assistant having to manually elevate the ribs, and without placing undue retraction force against the single rib immediately adjacent the incision, as would occur with an ordinary retractor rake.

In FIGS. 7–15, a set of rib rakes is illustrated. In each embodiment, the rib rake preferably is made from a single, integral metal strip stock. Preferably, the strip stock is approximately 2–4 cm wide, and more preferably about 3 cm wide. Preferably, the strip stock is approximately about 1.5 mm to about 3 mm thick, and more preferably is about 2 mm thick. The exact size of strip stock depends on the design criteria based upon the size of the patient upon which each rake is to be used, and the desires of the individual surgeon using each such rake.

Figure 8:
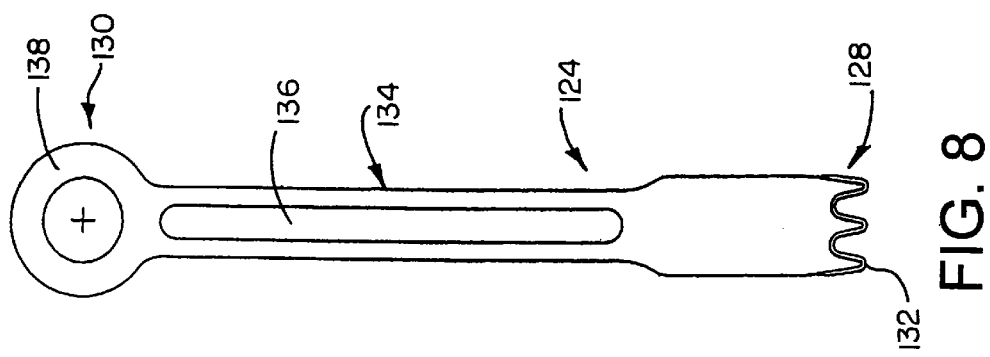
FIG. 8 is a front view of the dull tip rib rake of FIG. 7 in its preformed flat state.
Figure 7:
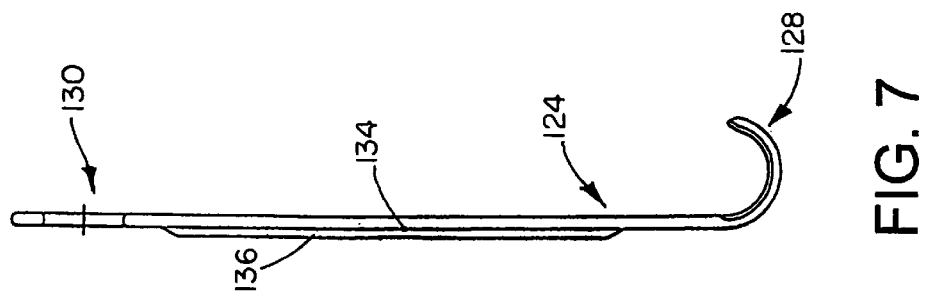
FIG. 7 is a side view of a small dull tip rib rake for initial retraction of a rib adjacent the intercostal incision in a mid-cab procedure, in accordance with an embodiment of the present invention.

Shown in FIG. 7 is a side view of a small dull tip rib rake 124 for initial retraction of a rib adjacent the intercostal incision in a mid-cab procedure. The rake 124 would preferably be initially placed in a smaller-boned patient in the initial retraction in a mid-cab procedure, when the initial intercostal incision had been made, but prior to enlarging the incision and harvesting of the internal mammary artery. Shown in FIG. 8 is a front view of the small dull tip rib rake 124 of FIG. 7 in its preformed flat state.

Figure 10:
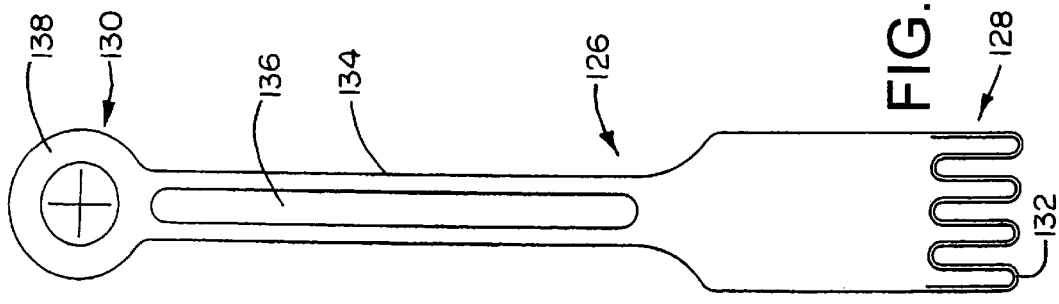
FIG. 10 is a front view of the dull tip rib rake of FIG. 9 in its preformed flat state.
Figure 9:
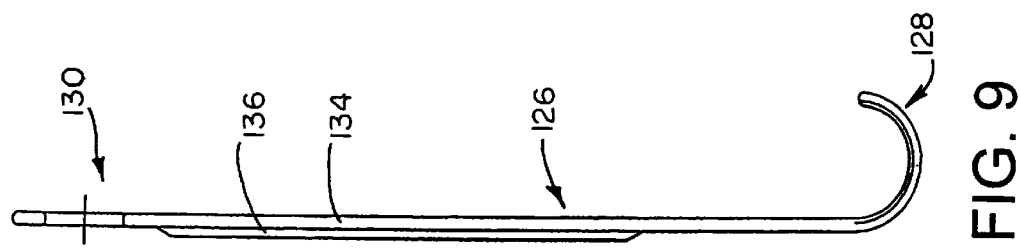
FIG. 9 is a side view of a larger dull tip rib rake for either initial or secondary retraction of a rib adjacent the intercostal incision in a mid-cab procedure in accordance with an embodiment of the present invention.

Shown in FIG. 9 is a side view of a larger dull tip rib rake 126 for either initial or secondary retraction of a rib adjacent the intercostal incision in a mid-cab procedure. FIG. 10 is a front view of the dull tip rib rake of FIG. 9 shown in its preformed flat state. The rake 126 is preferably used for initial placement in a larger-boned patient, but may also be used for secondary placement in a smaller-boned patient. Since the smaller dull tip rib rake 124 is, except for size, substantially similar to the larger dull tip rib rake 126, both will be described together in the following paragraphs. Except as to the indicated differences, the smaller rake 124 and the larger rake 126 are alike.

As shown in FIGS. 7–10, the dull tip rib rakes 124, 126, include a rake end 128 and a ring end 130. The rake end 128 includes dull rake teeth 132. In both rakes 124, 126, the rake teeth 132 have dull tips, as compared to conventional rakes for use with a conventional RULTRACT® retractor. The dull tips advantageously provide for adequate support of the ribs while preventing any injury to the rib to which the retractor is applied due to penetration which may otherwise occur from conventional very sharp rake tips. This novel adaptation is needed due to the relatively thin walls of the human rib as compared to the sternum, to which the conventional rakes are normally applied.

As shown in FIGS. 7–10, both rakes 124 and 126 include a shaft 134 between and connecting the rake end 128 and the ring end 130. The shaft 134 preferably includes an indented portion 136. The indented portion 136 of the shaft 134 provides additional strength to the rib rakes 124, 126. Each rib rake 124, 126 includes, preferably, a ring 138 for attaching the rib rake to a lifting device, such as the ratcheting winch assembly 50, suspended above the surgical site. Preferably, the ring 138 is attached to the lifting device by the snap clip 60 or other quickly releasable means for attaching the rake to the lifting device.

As shown in FIGS. 7 and 9, the rake end 128 preferably has a substantially round curvature. The rake end 128 preferably has a radius of curvature in the range from about 1 to about 3 cm, more preferably from about 1.5 to about 2 cm. Most preferably, in the larger rake 126, the rake end 128 has a radius of curvature of about 2 cm, and in the smaller rake 124, the rake end 128 has a radius of curvature of about 1.5 cm.

Additional differences, all relatively minor, between the smaller rake 124 and the larger rake 126 are as follows. A first difference between rakes 124 and 126 is that the larger rake 126 preferably includes four rake teeth 132, whereas the smaller rake 124 includes only three rake teeth 132. A second difference is that the rake teeth 132 on the smaller rake 124 are slightly narrower at the tip than are the rake teeth 132 on the larger rake 126. A third difference between the smaller rake 124 and the larger rake 126 is the length of the shaft 134, which is longer in the larger rake 126. A fourth difference, which may or may not be present, is that the shaft 134 may be slightly wider in the larger rake 126 than in the smaller rake 124.

Figure 11:
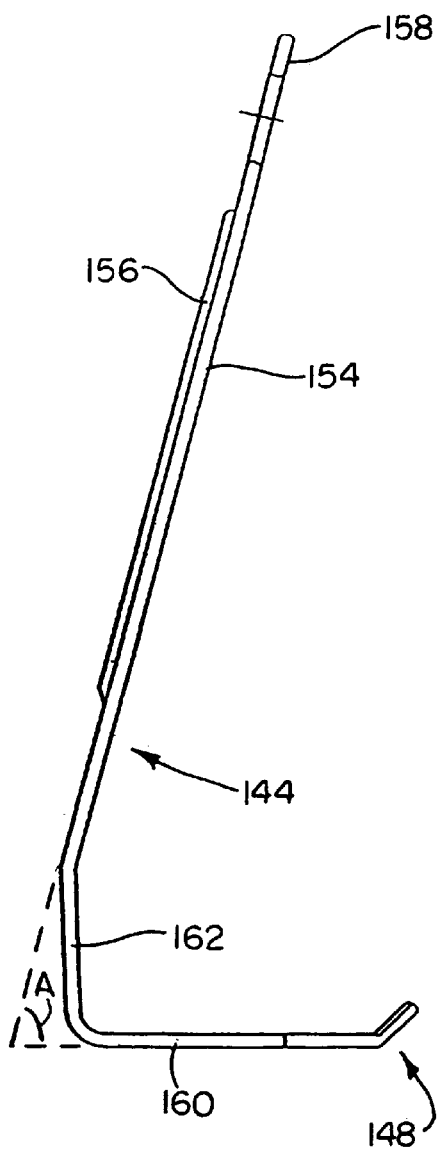
FIG. 11 is a side view of a flat tip medium rib rake for intermediate retraction of the ribs adjacent the intercostal incision in a mid-cab procedure in accordance with an embodiment of the present invention.
Figure 12:
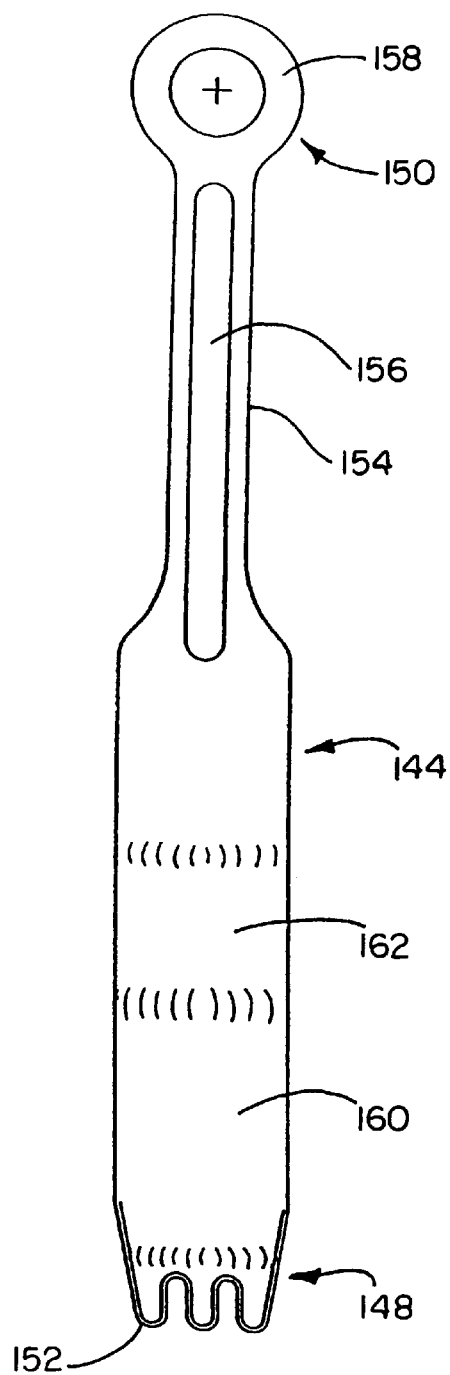
FIG. 12 is a front view of the flat tip medium rib rake of FIG. 11 in its preformed flat state.

FIG. 11 is a side view of a flat tip medium rib rake 144. The medium rib rake 144 is preferably used for an intermediate retraction of the ribs adjacent the intercostal incision during a mid-cab procedure, in accordance with an embodiment of the present invention. FIG. 12 is a front view of the flat tip medium rib rake of FIG. 11 in its preformed flat state.

Figures 13, 14:
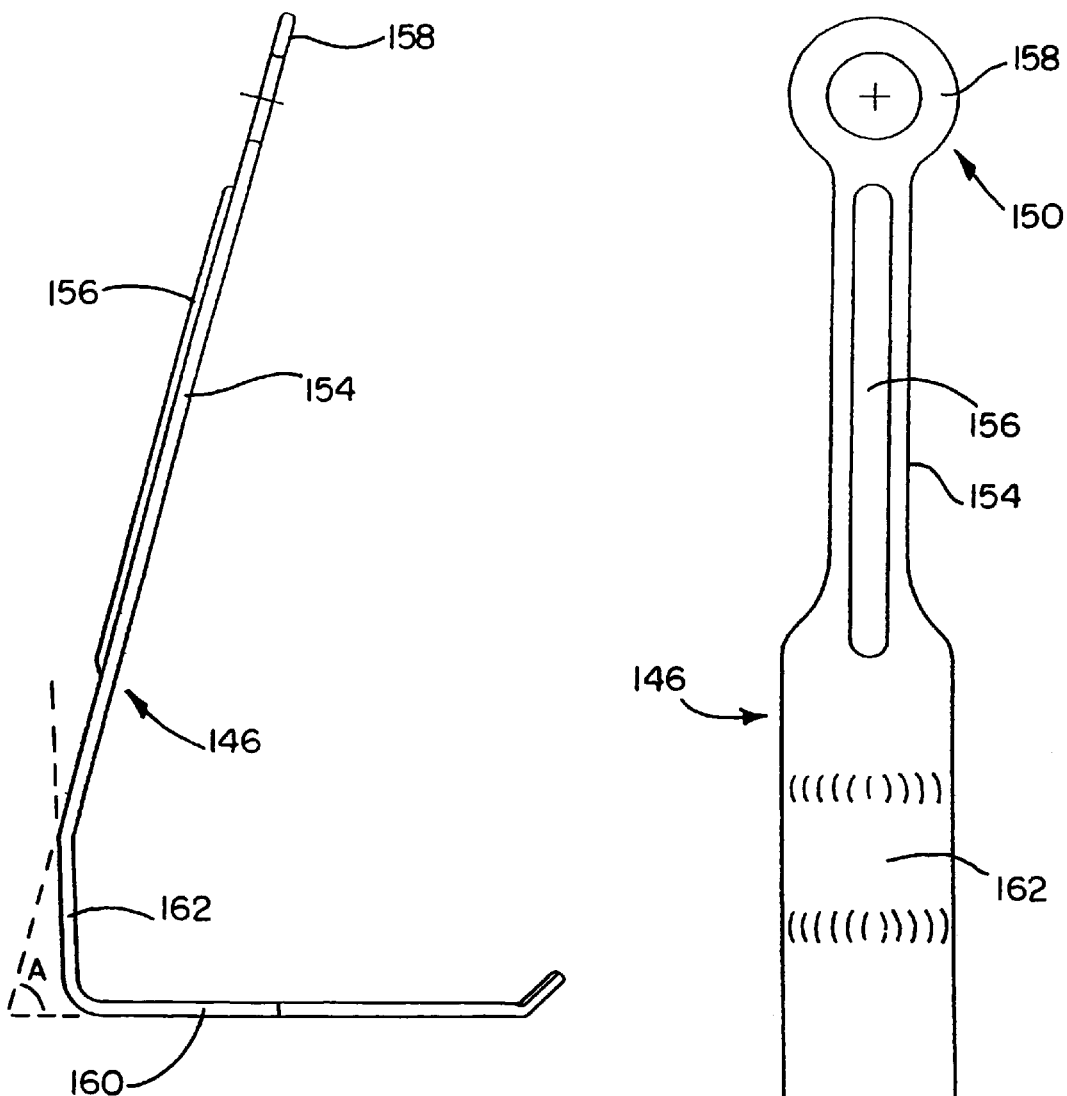
FIG. 13 is a side view of a flat tip long rib rake for full retraction of the ribs adjacent the intercostal incision in a mid-cab procedure in accordance with an embodiment of the present invention.
FIG. 14 is a front view of the flat tip long rib rake of FIG. 13 in its preformed flat state.

FIG. 13 is a side view of a flat tip long rib rake 146. The long rib rake 146 is preferably used for full or maximum retraction of the ribs adjacent the intercostal incision in a mid-cab procedure, in accordance with an embodiment of the present invention. FIG. 14 is a front view of the flat tip long rib rake of FIG. 13 in its preformed flat state. Since the medium flat tip rib rake 144 is, except for size, similar to the large flat tip rib rake 146, both will be described together in the following paragraphs. Except as to the indicated differences, the medium rake 144 and the large rake 146 are alike.

As shown in FIGS. 11–14, the flat tip rib rakes 144, 146, include a rake end 148 and a ring end 150. The rake end 148 includes flat rake teeth 152. In both rakes 144, 146, the rake teeth 152 have dull tips, as compared to conventional rakes for use with a conventional RULTRACT® retractor. The dull tips allow for adequate support of the ribs while preventing any injury to the rib to which the retractor is applied due to penetration which may otherwise occur from conventional very sharp rake tips. This is necessary due to the relatively thin walls of the human rib as compared to the sternum, to which the conventional rakes are normally applied.

As shown in FIGS. 11–14, both rakes 144 and 146 include a shaft 154 between and connecting the rake end 148 and the ring end 150. The shaft 154 preferably includes an indented portion 156. The indented portion 156 of the shaft 154 provides additional strength to the rib rakes 144, 146. Each rib rake 144, 146 includes preferably a ring 158 for attaching the rib rake 144, 146 to a lifting device, such as the ratcheting winch assembly 50, suspended above the surgical site. Preferably, the ring 158 is attached to the lifting device by the snap clip 60 or other quickly releasable means for attaching the rake to the lifting device.

As shown in FIGS. 11 and 13, the rake end 148 preferably has a substantially flat, straight base portion 160, which is connected to a substantially flat connecting portion 162. The connecting portion 162 is preferably oriented approximately perpendicular to the base portion 160. The connecting portion 162 is connected at its upper end to the shaft 154. Preferably, the angle A defined by the major extent of the shaft 154 relative to the major extent of the base portion 160 is less than 90°. More preferably, the angle A is between about 75° and 89°, and most preferably is about 80°. The angle provides security against the possibility that the rake 144, 146 will inadvertently slip out of the incision during the course of the surgery.

In the medium rake 144, the base portion 160 preferably has a length in the range from about 3 to about 6 cm, more preferably about 4 to about 5 cm, and most preferably about 4.5 cm. In the large rake 146, the base portion 160 preferably has a length in the range from about 5 to about 10 cm, more preferably in the range from about 6 to about 8 cm, and most preferably about 7 cm. In both the medium rake 144 and the large rake 146, the connecting portion 162 has a length or height in the range from about 2 to about 3 cm, more preferably about 2.5 cm. In both the medium rake 144 and the large rake 146, the shaft portion 154 has a length, from the bend at which the connecting portion 162 and shaft portion 154 meet to the region in which the ring 158 is attached to the upper end of the shaft portion 154, in the range from about 9 to about 15 cm, more preferably in the range from about 11 to about 13 cm, and most preferably about 12 cm.

As is shown in FIGS. 12 and 14, each of rakes 144 and 146 include, preferably, three rake teeth 152. The rake teeth 152, like the rake teeth 132 of the dull tip rakes 124 and 126, are not sharp, but instead are relatively dull at the tips. As with the dull tip rakes 124 and 126, the dull tips are to avoid unnecessary trauma to the tissues with which the rake will come in contact. As further shown in FIGS. 12 and 14, the strip stock from which the rakes are formed preferably tapers towards a narrower width profile in the region of the rake teeth 152. The taper provides, inter alia, for easier insertion into the incision and, like the dull rake teeth 152, for less unnecessary trauma to the surrounding tissues as a result. In addition, the rake teeth are angled upwardly with respect to the base portion 160 to assist in maintaining the base portion 160 under the ribs being supported thereby.

The primary difference between the medium rake 144 and the larger rake 146 is the length of the base portion 160. A second difference which is shown in FIGS. 12 and 14, is that the taper from the strip stock width to the rake teeth 152 is more gradual and extends over a greater length. Other differences may be found, but are not significant to the present invention.

Figure 15:
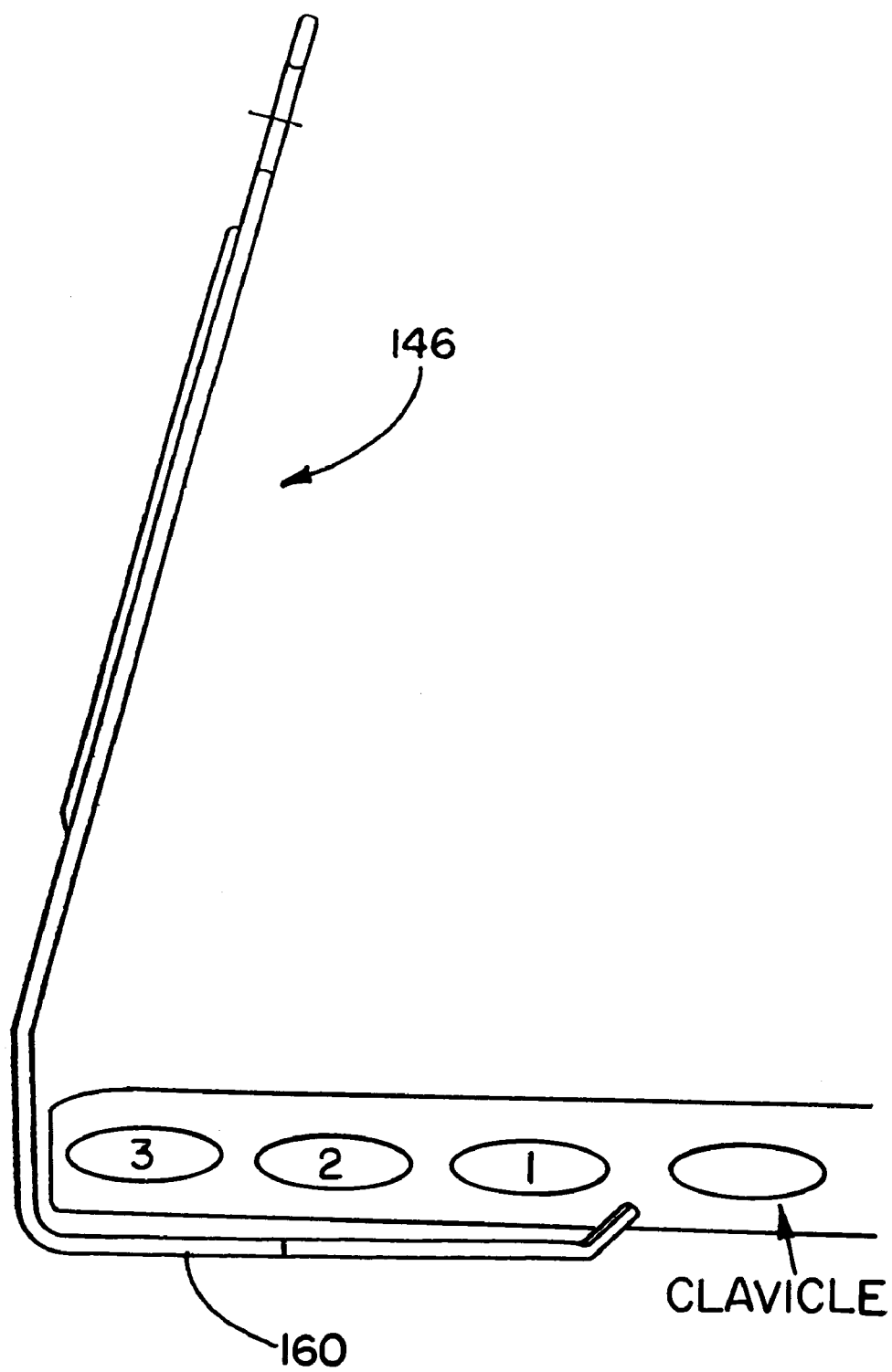
FIG. 15 is a schematic drawing of the flat tip long rib rake of FIGS. 13 and 14 in position in a patient's chest in accordance with the invention.

FIG. 15 is a schematic drawing of the flat tip long rib rake 146 of FIGS. 13 and 14 in position in a patient's chest, in accordance with the present invention, in a mid-cab procedure in which the incision was made in the third intercostal region. As shown, the long rib rake 146 provides support to the first three ribs adjacent the incision, when the incision has been made in the third, fourth or fifth intercostal region. Of course, if the incision had been made in the fourth intercostal region, ribs 4,3 and 2 would be supported rather than ribs 3,2 and 1.

The present invention provides a method for using the rib rakes in a surgical procedure. The method of retracting a patient's thoracic region during a thoracic surgical procedure, includes at least the following steps. First, the surgeon makes an incision in an intercostal region of the patient's thoracic region, preferably in the third, fourth or fifth intercostal region. Next, the surgeon applies a first dull tip rib retracting rake having a rounded support area to the patient's rib adjacent the incision, and retracts the rib to provide greater access to the incision. The surgeon begins the process of enlarging the surgical cavity in the patient's subthoracic region in a direction toward the patient's clavicle. When the incision has been partially enlarged, the first dull tip rib rake is removed, and a second dull tip rib rake having a flat support area of a first, medium size is applied to the patient's thoracic region and the supported area is again retracted. The surgeon then proceeds to further enlarge the surgical cavity. The method may include the additional steps of removing the second dull tip rib rake and then applying to the patient's subthoracic region a third dull tip rib retracting rake having a flat support area of a second, larger size, and again retracting the patient's thoracic region. Preferably, the method, in the step of enlarging the surgical cavity, includes a step of dividing the internal mammary artery from the patient's subthoracic region during the mid-cab. Preferably, in the method the step of making the incision is performed at the fourth or fifth intercostal region of the patient's thoracic region. Alternatively, the incision may be made at the third intercostal region of the patient's thoracic region.

This embodiment of the present invention, the xiphoid rake, may be used as the surgical retractor in any procedure which includes forming a surgical cavity similar to or by a xiphoid entry. The rake of this embodiment is particularly useful for retraction in a reoperative midsternotomy procedure in which a previous midsternotomy has been performed. In such cases, during healing from the first midsternotomy, a significant number of retrosternal adhesions may have formed between the site of the previous midsternotomy and underlying organs. In such case, it may be dangerous to the patient to perform a standard midsternotomy because of the adhesions.

In these cases, a new procedure has been developed in which an initial xiphoid entry is made. When access to the xiphoid process has been obtained, it is preferably excised, and a xiphoid rake according to the present invention is inserted at the point from which the xiphoid process was excised, and the whole sternum is retracted upwards and towards the patient's head. With the whole sternum thus retracted, the surgeon may proceed to dissect and divide the adhesions. In this procedure, the surgeon begins at the lower end of the sternum and gradually works towards the patient's head until the adhesions are completely dissected and the sternum is freed from the underlying organs and tissues.

In order to facilitate this task, at least three needs must be met. First, it is necessary to elevate the entire sternum. Second, it is necessary to provide unimpeded access to the cavity as it is opened further as the adhesions are taken down. Third, the xiphoid rake should not cause unnecessary trauma to the sternum. The novel xiphoid rake of the present invention meets all of these needs.

The conventional retractors are not adapted to perform the retraction of the entire sternum necessary to the xiphoid entry re-do procedure. In the conventional retractors, the rakes are smaller and have quite sharp tips on the rake teeth. The conventional rakes are relatively smaller since two rakes are attached to a single rake plate and both are normally used together to retract one side of the sternum which has been split by a midsternotomy. The conventional rakes have significantly sharper rake tips than does the xiphoid rake of the present invention since the rakes are normally applied to the newly incised edge of the midsternotomy incision, and need to "dig in" to the edge to maintain a sure grip thereon.

In accordance with a third embodiment of the present invention, a xiphoid rake is provided which is substantially larger and stronger than retractor rakes used for other procedures, and which includes a plurality of dull tipped rake teeth. The xiphoid rake is adapted to meet the requirements for retraction and elevation of the entire sternum during the reoperative or "re-do" coronary bypass procedure described above. The xiphoid rake is especially adapted for elevation of the entire sternum and attached ribs during the portion of the re-do procedure in which the adhesions between the inner side of the sternum and the underlying tissues are divided. Use of the xiphoid rake of the present invention avoids numerous problems previously associated with use of a single conventional rake to elevate the sternum during this portion of the re-do procedure.

In addressing the problem of lifting the entire sternum during the re-do procedure, the xiphoid rake has been extensively modified from conventional retractor rakes. The xiphoid rake is significantly stronger overall and includes a longer body-supporting portion for providing the greater sternal support required to lift a substantial portion of the sternum and chest on a single rake as the process of dissecting the adhesions is carried out. The sternal supporting portion of the xiphoid rake is wider than in conventional rakes. The rake tips of the xiphoid rake are broader and significantly less sharp than are the tips of conventional retractor rakes.

The second problem addressed by this invention is solved by the elimination in conventional mechanisms of the standard rake plate and the second, and sometimes third, rake which is unused in the xiphoid entry. To this end, preferably the xiphoid rake includes a ring portion for direct attachment to a lifting device. Preferably, the lifting device includes a snap clip for allowing quick attachment and release of each rake and does not include the standard retractor plate. More preferably, the lifting device includes a swivel device attaching the snap clip to the lifting device. The lifting device may be the same mechanism as described in the above-mentioned patent. In the surgical procedure, once the adhesions have been cleared, the rake is removed and the standard midsternotomy may be safely performed, and the coronary bypass or other thoracic procedure may then be performed as in a case in which no previous midsternotomy has been performed.

Figures 16, 17, 18:
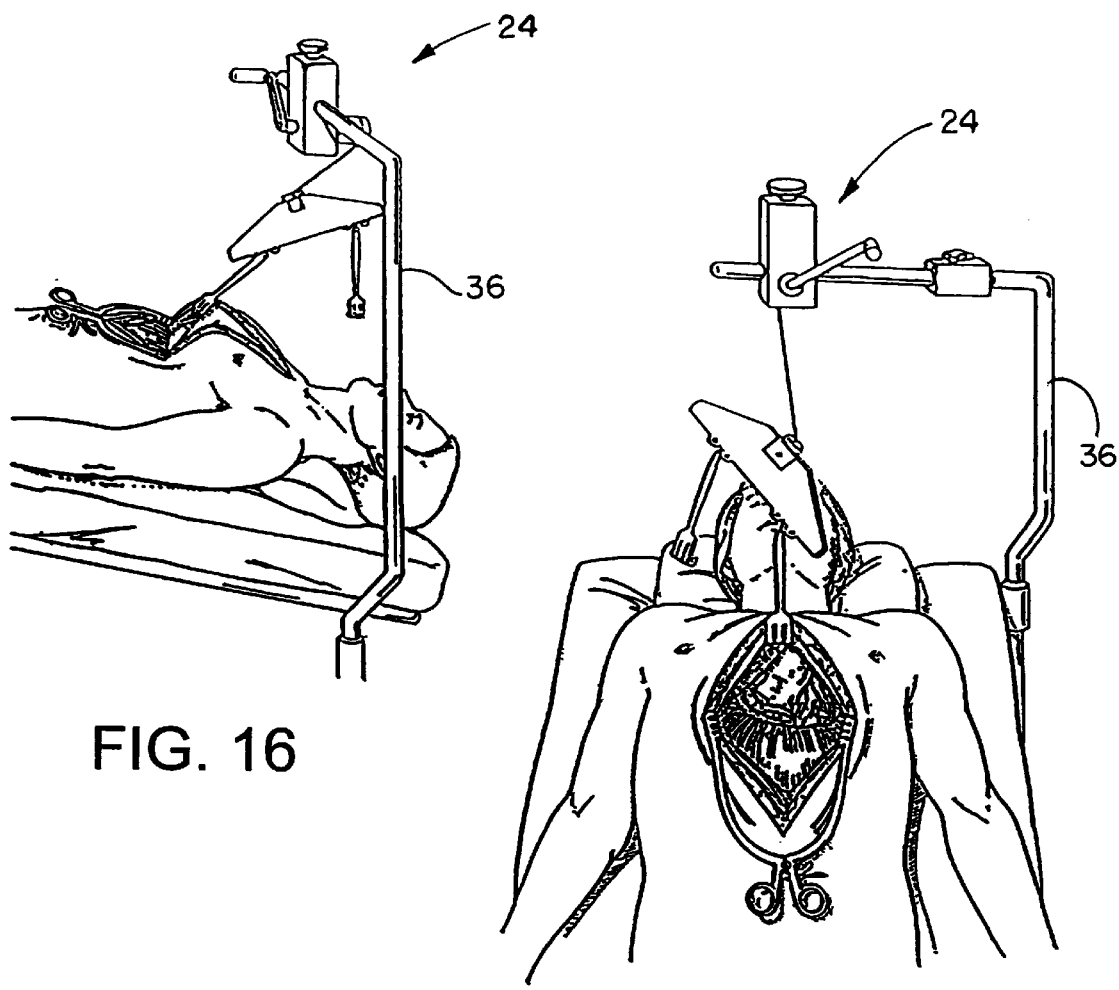
FIG. 16 is a view from the patient's side of a conventional retractor plate assembly and standard rakes as may be applied to a patient during a xiphoid entry surgery.
FIG. 17 is a view from the patient's foot of a conventional retractor plate assembly and standard rakes as may be applied to a patient during a xiphoid entry surgery.
FIG. 18 is a view from the patient's side of the xiphoid rake in accordance with the present invention as may be applied to a patient during a xiphoid entry surgery.

The foregoing procedure has previously been performed by using a standard retractor with a retractor plate and two rakes, with only one rake applied to lift the entire sternum. This was less than satisfactory for several reasons. First, as shown in FIGS. 16 and 17, the presence of the retractor plate in the operative field provides an unnecessary obstruction to the surgeon and surgical team. In any surgery, and particularly in thoracic surgery, the operative field must be kept as clear as possible, and the presence of the retractor plate and second rake is inconsistent with this need. Second, as shown in FIGS. 16 and 17, the line connecting the lifting device, the retractor plate and the rake is not straight, which results in the lifting force being applied to the sternum in a direction other than vertical, thereby imparting an undue torque to the sternum.

By using the xiphoid rakes and snap clip of the present invention, as shown in FIG. 18, the operative field is much less obstructed and the angle of lift applied to the sternum can be precisely controlled by the surgeon.

Referring now to FIGS. 19–22, there is shown first and second xiphoid rakes 174 and 176 in accordance with a third embodiment of the present invention. FIG. 19 shows the first xiphoid rake 174. FIG. 20 is a frontal view of the xiphoid rake 174 of FIG. 19 in its preformed flat state. FIG. 21 shows the second, or alternative, xiphoid rake 176 in accordance with the invention. FIG. 22 is a frontal view of the xiphoid rake 176 of FIG. 21 in its preformed flat state. The first and second xiphoid rakes are substantially the same. The relatively minor differences between the xiphoid rakes will be pointed out in the following.

The first xiphoid rake 174 preferably includes four rake teeth. The second xiphoid rake 176 preferably includes only three teeth. In both embodiments, more or fewer rake teeth may be included. As shown in FIGS. 20 and 22, the rake teeth of the xiphoid rakes are considerably longer than the rake teeth of other retractor rakes. The additional length requires that the material from which the xiphoid rake is made have greater strength.

As shown in FIGS. 19–22, both xiphoid rakes 174 and 176 include a rake end 178 and a ring end 180, and further include a shaft 182 between and connecting the rake end 178 to the ring end 180. The shaft 182 preferably does not include an indented portion as in the rib rakes described above. Each xiphoid rake 174, 176 preferably includes a ring 184 for attaching the xiphoid rake 174, 176 to a lifting device, such as the ratcheting lifting device 24, suspended above the surgical site. Preferably, in use the ring 184 is attached to the lifting device by a snap clip or other quickly releasable means for attaching the rake to the lifting device. More preferably, in use the ring 184 is attaching to the lifting device by a snap clip or other means which is swivelably mounted on the cable 32 from the lifting device.

As shown in FIGS. 19 and 21, the rake end 178 preferably has a flattened base portion 186 including a central flat section. The base portion 186 is connected by a relatively large radius curved section 188 to a substantially flat connecting portion 190. The entirety of the xiphoid rakes 174, 176 are preferably made from a single strip of metal stock.

Thus, the connecting portion 190 is an integral part of both the shaft 182 and the base portion 186. Both the connecting portion 190 and the shaft 182 are preferably oriented approximately perpendicular to the central portion of the base portion 186. Preferably, the angle at which the shaft 182 and the connecting portion 190 meet the base portion 186 is approximately equal to or slightly less than about 90°. More preferably, the angle at which the shaft 182 and the connecting portion 190 meet the base portion 186 is slightly less than 90°.

In the first xiphoid rake 174, as shown in FIG. 19, the tips 192 of the rake teeth 194 are curved such that the teeth are oriented slightly upward from the plane defined by the flat part of the base portion 186. The radius of curvature of the tips of the rake teeth 194 preferably is approximately equal to the radius of curvature of the curved portion 188.

In the xiphoid rake 174, the flat cental part of the base portion 186 preferably has a length in the range from about 1 to about 3 cm, more preferably about 1.5 to about 2.5 cm, and most preferably about 2 cm. The overall length of the rake teeth of the xiphoid rake 174, as best shown in FIG. 20, is in the range from about 3 to about 7 cm, more preferably about 5 cm.

In the second xiphoid rake 176, the flat part of the base portion 186 preferably has a length in the range from about 1.5 to about 5 cm, more preferably in the range from about 2 to about 3 cm, and most preferably about 2.5 cm. As shown in FIG. 21, in the xiphoid rake 176, the flat part of the base portion 186 is somewhat longer than in the first rake 174, and the rake teeth 194 are angled upward from the plane defined by the base portion 186 rather than curved upward.

In both the xiphoid rakes 174 and 176, the connecting portion 190 has a length or height in the range from about 2 to about 3 cm, more preferably about 2.5 cm. In both rakes, the connecting portion preferably tapers from the width of the rake teeth down to the width of the shaft 182, as best shown in FIGS. 20 and 22.

In both the xiphoid rakes 174 and 176, the shaft portion 182 has a length, from the bend at which the connecting portion 190 and shaft portion 182 meet to the region in which the ring 184 is attached to the upper end of the shaft portion 182, in the range from about 6 to about 14 cm, more preferably in the range from about 8 to about 10 cm, and most preferably about 9 cm.

As is shown in FIGS. 20 and 22, each of rakes 174 and 176 include, preferably, dull tipped rake teeth 194. Thus, the rake teeth of the xiphoid rake, like the rake teeth 132 of the dull tip rakes 124 and 126, and the rake teeth 152 of the rib rakes 144 and 146, are not sharp, but instead are relatively dull. As with the other dull tip rakes, the dull tips 192 of the xiphoid rakes help to avoid unnecessary trauma to the tissues with which the rake will come in contact.

Figure 23:
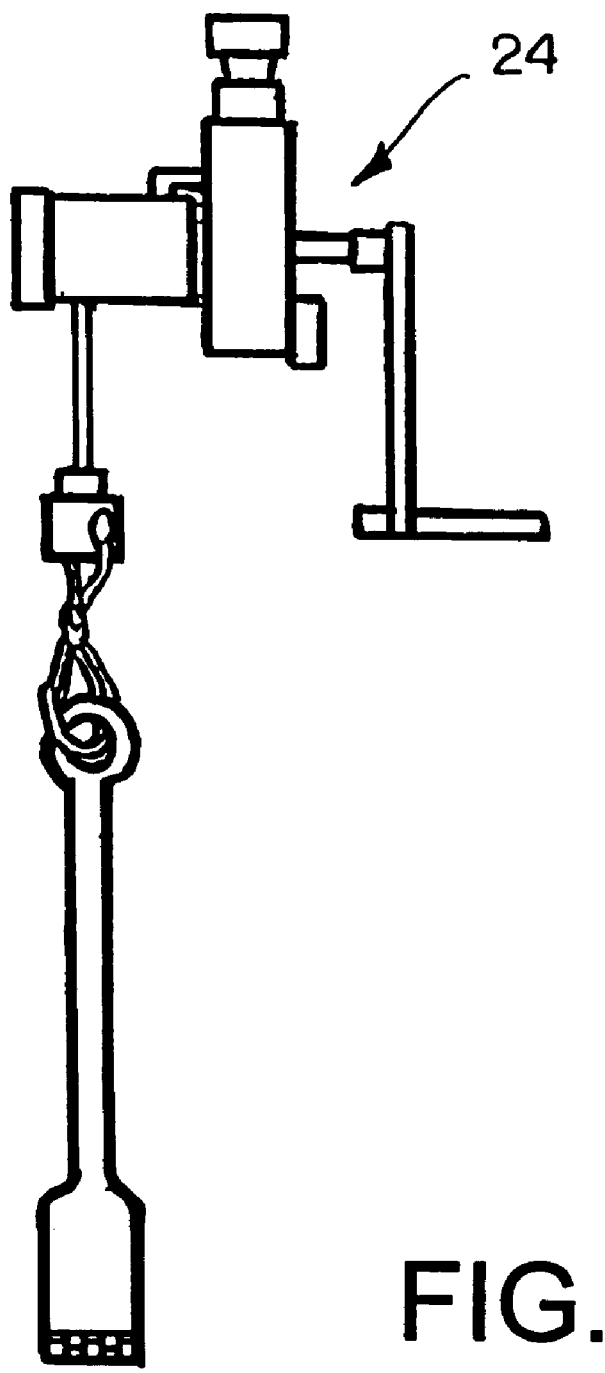
FIG. 23 is a side elevational view of a xiphoid rake in accordance with the invention attached to a lifting device by a swivel connection and a snap clip.

FIG. 23 is a side elevational view of a xiphoid rake in accordance with the invention attached to a lifting device by a swivel connection and a snap clip, similar to FIG. 2.

Preferably, as suggested in FIGS. 19 and 21, strip stock from which the xiphoid rakes 174,176 are formed is approximately about 1.5 mm to about 3 mm thick, and more preferably is about 2 mm thick. As shown in FIGS. 20 and 22, the width of the strip stock varies, but is generally cut from stock initially in the range from about 2 to about 5 cm wide. The exact size of strip stock depends on the design criteria based upon the size of the patient upon which each rake is to be used, and the desires of the individual surgeon using each such rake.

As shown in FIG. 18, when the xiphoid rake, together with the swivel and snap clip attachments to the lifting device are used, the surgical field in which the surgeon and surgical team must operate is significantly less crowded as compared to the situation shown in FIGS. 16 and 17.

The entire preferred xiphoid rake retraction system is shown in FIG. 23. Preferably, as described herein above, the xiphoid rake retraction system includes a ratcheting lifting device, a cable, a swiveling connecting section, a snap clip connector, and the xiphoid rake 174 (or 176). Preferably, the ratcheting lifting device is the same device used with the RULTRACT® retractor, as shown in FIG. 1.

The present embodiment of the invention is employed in a surgical procedure, and the following method is exemplary describing generally the steps in using the xiphoid rake of the present invention. The method is designed for and will be set forth in the embodiment of performing a reoperative midsternotomy on a patient having undergone a previous midsternotomy procedure. The method includes the initial step of making an incision in a patient's thoracic-abdominal region near the patient's xiphoid process. Preferably, this incision is made along the scar from the previous midsternotomy. The wires or other reaftchment devices, such as non-disintegrating sutures, used to reattach the sternum in the previous procedure, are removed. Preferably, the xiphoid process is excised at this time. Possibly, the xiphoid process may not be excised, if the surgeon deems it is strong enough to support the patient's sternum. Next, the surgeon applies a dull tip xiphoid rake having a support area to the patient's sternum to the xiphoid process, or to the site from which the xiphoid process was excised, such that the support area extends under the sternum to provide a lifting force to the sternum. A retracting force is applied to retract the xiphoid rake whereby the entire sternum and attached ribs are retracted in a direction upward and toward the patient's head. At this time, the surgeon can begin to enlarge the surgical cavity in the patient's substernal region, by dissecting and dividing the adhesions connecting the substernal surface to the underlying organs and tissues. The surgeon proceeds to enlarge the cavity moving in a direction toward the patient's head. When the adhesions have been completely divided, the xiphoid rake is removed, and the sternum is split by the usual sternal saw, following which the coronary bypass procedure, or other thoracic surgical procedure, may be undertaken.

The present invention further provides a system for retracting a patient's entire sternum in a surgical procedure. The system includes at least the following elements. First the system includes a lifting device having the ratcheting lifting device 24, such as that shown in FIGS. 1, 2 and 23. As shown in the figures, a cable having proximal and distal ends is attached at its proximal end to the lifting device such that it may be retracted by the lifting device and stopped in selected positions by the ratcheting portion of the device. The system further includes a swiveling connecting section attached to the distal end of the cable, and a snap clip connector attached to the swiveling section. This connection allows the snap clip to rotate in relation to the lifting device. The relatively free rotation of the swivel and snap clip prevents placing any torque on the xiphoid rake. Finally, the system includes a xiphoid rake having a rake end and a ring end for releasably attaching to the snap clip. The system thus described may be utilized to retract a patient's entire sternum in a surgical procedure. Preferably, the system is used for a re-do midsternotomy, in which the patient has undergone a previous sternotomy. Preferably, the procedure which includes the midsternotomy is a coronary bypass procedure, but it may include any thoracic surgical procedure which requires a subsequent midsternotomy after an initial midsternotomy has been performed on the same patient.

Although the invention has been shown and described with respect to certain embodiments, it is obvious that equivalents and modifications will occur to others skilled in the art upon the reading and understanding of the specification. The present invention includes all such equivalents and modifications, and is limited only by the scope of the following claims.

What is claimed is:

1. A method of performing a reoperative midsternotomy on a patient having undergone a previous midsternotomy procedure, including the steps of:

making an incision in a patient's thoracic-abdominal region near the patient's xiphoid process;

removing any reattachment devices from the sternum remaining from the previous procedure;

applying a xiphoid rake having a support area to the patient's sternum near an attachment point of the patient's xiphoid process;

applying a retracting force to the xiphoid rake;

enlarging the surgical cavity in the patient's substernal region in a direction toward the patient's head;

removing the xiphoid rake;

splitting the patient's sternum and proceeding with a thoracic surgical procedure.

2. The method of claim 1, wherein the incision is made along the scar from the previous midsternotomy.

3. The method of claim 1, wherein preceding the step of applying the xiphoid rake, the patient's xiphoid process is excised.

4. A xiphoid retraction system, comprising:

a ratcheting lifting device, a cable having proximal and distal ends, wherein the cable is attached at its proximal end to the lifting device such that it may be retracted by the lifting device and stopped in selected positions by a ratcheting device;

a swiveling connecting section attached to the distal end of the cable;

a snap clip connector attached to the swiveling section such that the snap clip is enabled to rotate in relation to the lifting device; and a xiphoid rake having a rake end and a ring end, the ring end being adapted for releasably attaching to the snap clip, whereby the system may be utilized to retract a patient's entire sternum in a surgical procedure.

5. The xiphoid retraction system of claim 4, wherein the rake comprises three rake teeth.

6. The xiphoid retraction system of claim 4, wherein the rake comprises four rake teeth.

7. The xiphoid retraction system of claim 4, wherein the xiphoid rake further comprises an elongated shaft and a base portion, and an angle between the elongated shaft and the base portion is less than 90°.

8. The xiphoid retraction system of claim 4, wherein the xiphoid rake further comprises an elongated shaft having a length in the range from about 6 to about 14 cm.

9. The xiphoid retraction system of claim 4, wherein the xiphoid rake further comprises a base portion with a central portion having a length in the range from about 1 to about 3 cm.

10. The xiphoid retraction system of claim 4, wherein the xiphoid rake further comprises a base portion with a central portion having a length in the range from about 1.5 to about 5 cm.

11. The xiphoid retraction system of claim 4, wherein the xiphoid rake further comprises rake teeth having a length in the range from about 3 to about 7 cm.

* * * * *